United States Patent
Bally et al.

(10) Patent No.: US 6,837,876 B2
(45) Date of Patent: Jan. 4, 2005

(54) DEVICE FOR ADMINISTERING AN INJECTABLE PRODUCT IN DOSES

(75) Inventors: Christoph A. Bally, Bussy St Georges (FR); Stefan Jost, Bolligen (CH)

(73) Assignee: TecPharma Licensing AG, Burgdorf (CH)

( * ) Notice: Subject to any disclaimer, the term of this patent is extended or adjusted under 35 U.S.C. 154(b) by 244 days.

(21) Appl. No.: 10/273,137

(22) Filed: Oct. 16, 2002

(65) Prior Publication Data

US 2003/0105429 A1 Jun. 5, 2003

Related U.S. Application Data

(63) Continuation of application No. PCT/CH01/00212, filed on Apr. 3, 2001.

(30) Foreign Application Priority Data

Apr. 17, 2000 (DE) .......................................... 100 18 924

(51) Int. Cl.[7] .............................................. A61M 5/00
(52) U.S. Cl. ....................... 604/207; 604/131; 604/156; 604/134; 604/135; 604/136
(58) Field of Search ................................. 604/131, 156, 604/134–136, 157, 211, 218, 232, 233, 151, 152, 154, 181, 187, 207–209, 224, 227; 222/336, 327, 386, 43, 309, 283, 288, 32, 36, 37, 38, 325, 326

(56) References Cited

U.S. PATENT DOCUMENTS

| | | | |
|---|---|---|---|
| 2,750,943 A | 6/1956 | Dann | |
| 3,051,172 A | 8/1962 | Bruchhaus | |
| 3,504,673 A | 4/1970 | Parisi | |
| 5,865,804 A | 2/1999 | Bachynsky | |
| 5,975,355 A | 11/1999 | Cecala et al. | |
| 2002/0029018 A1 * | 3/2002 | Jeffrey | 604/209 |

FOREIGN PATENT DOCUMENTS

| | | |
|---|---|---|
| CH | 682722 | 11/1993 |
| FR | 1528444 | 11/1968 |

* cited by examiner

Primary Examiner—Brian L. Casler
Assistant Examiner—Cris L Rodriguez
(74) Attorney, Agent, or Firm—Dorsey & Whitney LLP

(57) ABSTRACT

A device for administering an injectable product in doses, wherein the device includes a casing, a reservoir for the product, a piston, an advancing element which moves the piston a selected path length, and a dosing mechanism including a number of dosing bodies and a dosing element operable to move the dosing bodies, wherein the path length is selected by the dosing element moving at least one dosing body between the piston and the advancing element.

15 Claims, 5 Drawing Sheets

DEVICE FOR ADMINISTERING AN INJECTABLE PRODUCT IN DOSES

PRIORITY CLAIM

This application is a Continuation of International Application No. PCT/CH01/00212 filed on Apr. 3, 2001, which claims priority to German Patent Application No. DE 100 18 924.5, filed Apr. 17, 2000, both of which are incorporated herein by reference.

BACKGROUND

The present invention relates to devices for administering an injectable product in doses.

Injectable products, particularly medicinal fluids, often need to be administered in doses. Mechanical and/or electronic dosing is often complicated and drives up the price of the devices used to inject doses. Furthermore, dosing errors can occur, particularly in the case of manual dosing. In order to avoid dosing errors, the user has to dose with a sensitive use of force.

SUMMARY

The invention has the object of providing a device for administering an injectable product in doses, wherein the device increases safety. A desired dosage of the product is actually set during dosing. Further objects are providing a cost-effective and operationally reliable injection device, and simple, manual dosing.

In one embodiment, the present invention comprises an injection device comprising a piston, an advancing element, and a dosing mechanism comprising a number of dosing bodies and a dosing element, wherein a dose is set by operably inserting at least one dosing body generally between the piston and the advancing element by means of the dosing element.

In one embodiment, the present invention comprises a device for administering an injectable product in doses, comprising a casing comprising a reservoir for the product, a piston which, when shifted in an advancing direction towards an outlet of the reservoir, forces product out of the reservoir, a delivery means comprising an advancing element which presses the piston in the advancing direction by a set path length, and a dosing means comprising a number of dosing bodies and a dosing element, wherein the path length is defined by at least one dosing body which is inserted between the piston and the advancing element by means of the dosing element, before the delivery means is activated.

A device in accordance with the invention for administering an injectable product in doses includes a casing comprising a reservoir, a piston, a delivery means and a dosing means. The reservoir is preferably formed by an ampoule in which an injectable product is situated. When shifted in an advancing direction towards an outlet of the reservoir, the piston forces product out of the reservoir. The product is dosed by setting a path length by which the piston can be shifted at most when activated.

Via an advancing element, the delivery means presses the piston in the advancing direction by the path length set. The dosing means includes a number of dosing bodies and a dosing element. The path length is defined by the number and thickness or thicknesses of the dosing bodies which are inserted between the piston and the advancing element before the next administering in each case. Simple, easily verifiable and, therefore, safe dosing is enabled for a user.

In one embodiment, the advancing element is accommodated in the casing such that it may be linearly shifted in the advancing direction of the piston, and is formed by a button or sleeve. The dosing element is formed by an element which may be linearly shifted, for example, a button or sleeve. It protrudes out of the casing. In some embodiments, the advancing element and the dosing element are both respectively held pre-tensioned in a starting position. The advancing element and the dosing element are activated counter to this holding force. It is thus possible to automatically return said elements to the starting position.

The dosing element can be moved back and forth between two end positions. One end position is the starting position. The dosing element assumes the other, front end position when it has moved a dosing body into the dosing position. A fixing structure for the dosing body in the dosing position can take the form of a front stopper for the dosing element in the front end position. A front stopper can, however, also be directly formed on the dosing element. Once it is abutting the front stopper, i.e., a front stopper for the dosing body or a front stopper directly on the dosing element, the dosing element can only be moved back again towards its starting position. Dosing by means of a dosing element which may be moved back and forth is particularly safe.

A device can be provided which only enables a restoring movement by the dosing element once a dosing body has been fully inserted into a dosing position between the piston and the advancing element. To this end, a catch can be used which prevents a restoring movement until the dosing element has reached a front end position in which a dosing body abuts the front stopper restricting the movement. A dosing element can be pressed or pulled into the dosing position on a curved rail or linearly.

In one embodiment, the dosing bodies are moved, in particular slid, into the dosing position between the piston and the advancing element perpendicular to the advancing direction of the piston. Alternatively, the dosing bodies can be displaced in the delivering direction, between the piston and the advancing element, away from a stockpile. When the dosing bodies are displaced in the delivering direction, the stockpile can in particular be arranged offset along the length of the longitudinal axis of the reservoir. The dosing bodies are moved into the dosing position against a stopper. When a dosing body is moved, the dosing element presses loosely against the dosing body, i.e., the dosing element pressing against the dosing body is the only connection between the dosing element and the dosing body in each case.

In some embodiments, the dosing bodies are piled loosely one on top of the other, in the advancing direction between the piston and the advancing element. They are guided in the dosing position by the casing. When the delivery means is activated, they are slid into the reservoir and then guided by the inner surface area of the reservoir. A number of dosing bodies are moved into the dosing position, by laterally sliding them over each other. The dosing bodies can be tapered in their shifting direction, in order to facilitate sliding them over each other.

In some embodiments, laminae are used as the dosing bodies. Particularly preferably, flat laminae having a small thickness are used. The sum of the thicknesses of the dosing bodies inserted between the piston and the advancing element defines the path length and, therefore, the dosage. The thickness of one dosing body is the smallest path length which may be set. The dosing bodies preferably each have the same thickness. They can be lenticular or cylindrical or can assume other shapes. The dosing bodies can exhibit one flattened side or two flattened sides. This improves linear guiding.

In some embodiments, the dosing bodies are accommodated in a magazine, piled one on top of the other into a stockpile of dosing bodies, for stockpiling before dosing. The magazine may be integrated into the casing. When the dosing element moves perpendicular to the stockpile, the dosing element displaces one of the dosing bodies away from said stockpile into the dosing position between the piston and the advancing element.

The stockpile is pressed against a stopper by a pre-tensioned spring. Laterally guiding the stockpile is taken care of by the magazine. The stopper and the lateral guide co-operate in such a way that exactly one dosing body is released for one perpendicular shift. For this purpose, there can be a distance between the lateral guide and the stopper, or the lateral guide is open worked such that the dosing element can be engaged with an outermost dosing body of the pile. Once this dosing body has moved into the dosing position, the spring presses the stockpile one position further so that a dosing body again abuts the stopper and is free to be perpendicularly displaced from the stockpile.

In some embodiments, the magazine is laterally offset, along the reservoir. In some embodiments, it is also axially at the same height as the reservoir.

In one embodiment, the dosing body is linearly shifted, perpendicular to the stockpile and perpendicular to the advancing direction of the piston, away from the stockpile between the piston and the advancing element. For inserting them between the piston and the advancing element, the dosing bodies are advantageously guided on a rail. The stopper also forms a guide for a dosing body while it is moved away from the stockpile between the piston and the advancing element. The stopper guides a dosing body on its covering surface.

While a dosing body is being inserted between the piston and the advancing element, the dosing element and the stopper are slid at least partially over and/or into each other. The dosing element acts on a lateral surface of the dosing body, preferably via a tongue, in order to move it away from the stockpile. The stopper is formed in the shape of a prong and holds a dosing body only at its respective lateral edge areas. The dosing element acts in the central area of the dosing body and is slid into the prong-shaped stopper when the dosing body is shifted. In some embodiments, the tongue of the dosing element exhibits a larger thickness than an individual dosing body.

One or more dosing bodies are held pre-tensioned in the dosing position. The pre-tensioning force is then less than the static frictional force of the piston in the reservoir. Because the dosing bodies are pre-tensioned, they cannot jam in the dosing position. The advancing element can be elastically tensioned in the advancing direction and thus press the dosing body or bodies situated in the dosing position towards the piston. In one embodiment, a clamp is provided which may be moved relative to the advancing element and which is pressed in the advancing direction towards the piston by an elastically acting tension force and, when a dosing body is inserted into the dosing position, is moved against the tension force and counter to the advancing direction. The elastically acting tension force is generated by a spring which presses or pulls the clamp in the advancing direction. One end of the clamp, which presses on a dosing body, is formed in such a way that a dosing body pressing from one side moves the clamp counter to the tension force acting on it.

In one development of the invention, the dosing bodies moved into the dosing position prior to delivery are counted in a counter, and the number of them is displayed on a display. The counter is preferably re-set to zero during a delivery process. The counter comprises one or more contacts which the dosing element and/or the advancing element can slide over.

The invention is primarily of use in mobile devices, such as injection pens, but can also advantageously be used in stationary devices.

DETAILED DESCRIPTION

Figure 1:
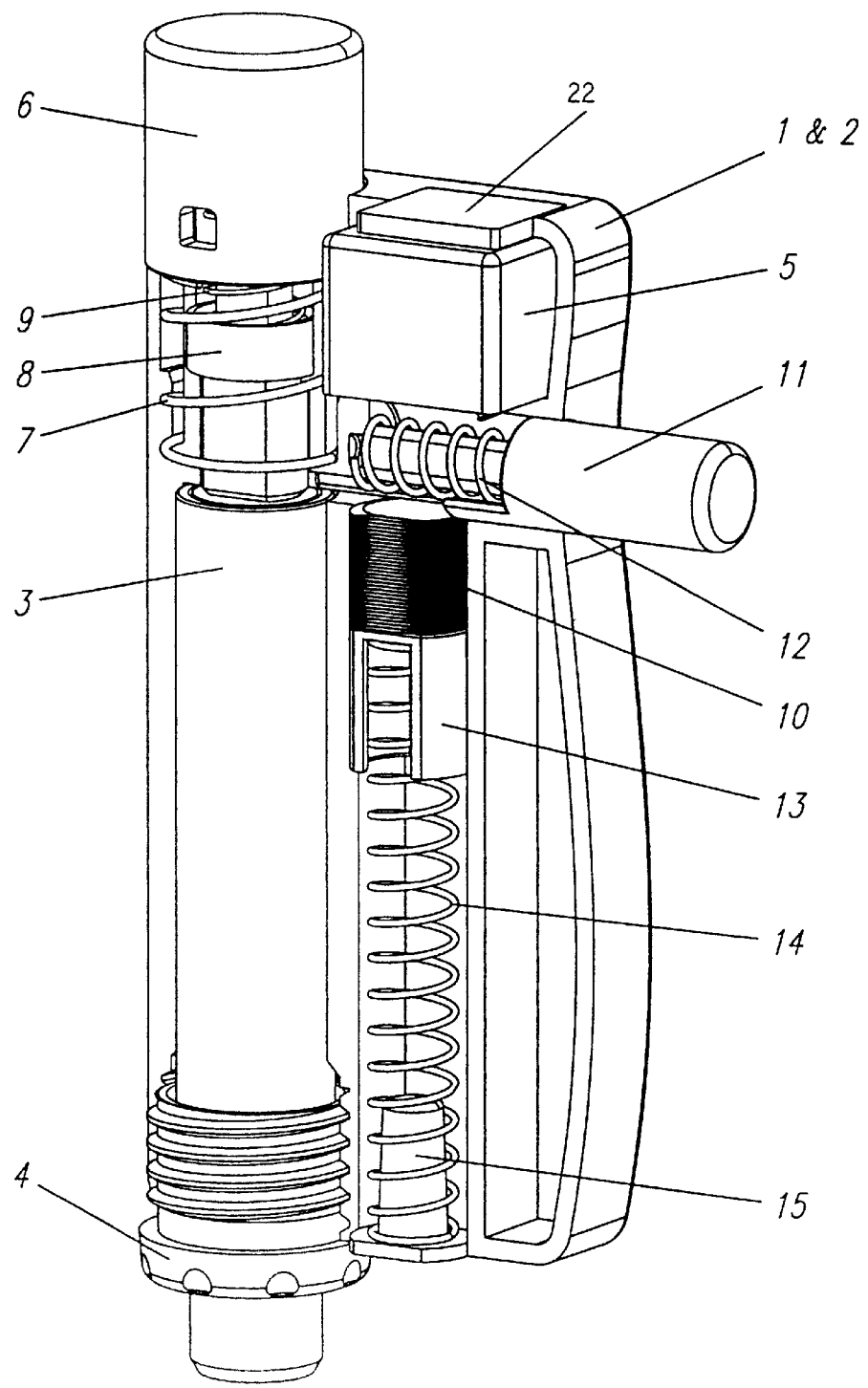
FIG. 1 is a partially cut-away perspective view of a device in accordance with the present invention.

FIG. 1 shows a device in accordance with the present invention in a three-dimensional view. A casing 1 consists of two shells 2, only one of which is shown in FIG. 1. The second shell is symmetrically arranged relative to the incision axis. A reservoir 3, termed an ampoule in the following, is accommodated in the casing 1 and held fixed by means of a cover 4 or adapter 4. Laterally offset parallel to the ampoule 3, individual dosing bodies 10 are collectively accommodated, piled on top of each other in a pile of dosing bodies, in a magazine 26 in the casing. The dosing bodies 10 there are situated in a stock or stockpiled position. A dosing means comprising a dosing element 11 and a tensioning element 12 is arranged above the pile of dosing bodies or stockpile. Above the ampoule 3, a delivery means comprising an advancing element 6 and a tensioning element 7 is mounted by the casing 1. Furthermore, a counter 5 and a display 22 are situated in the casing, wherein the display 22 can be read from without.

Figure 2:
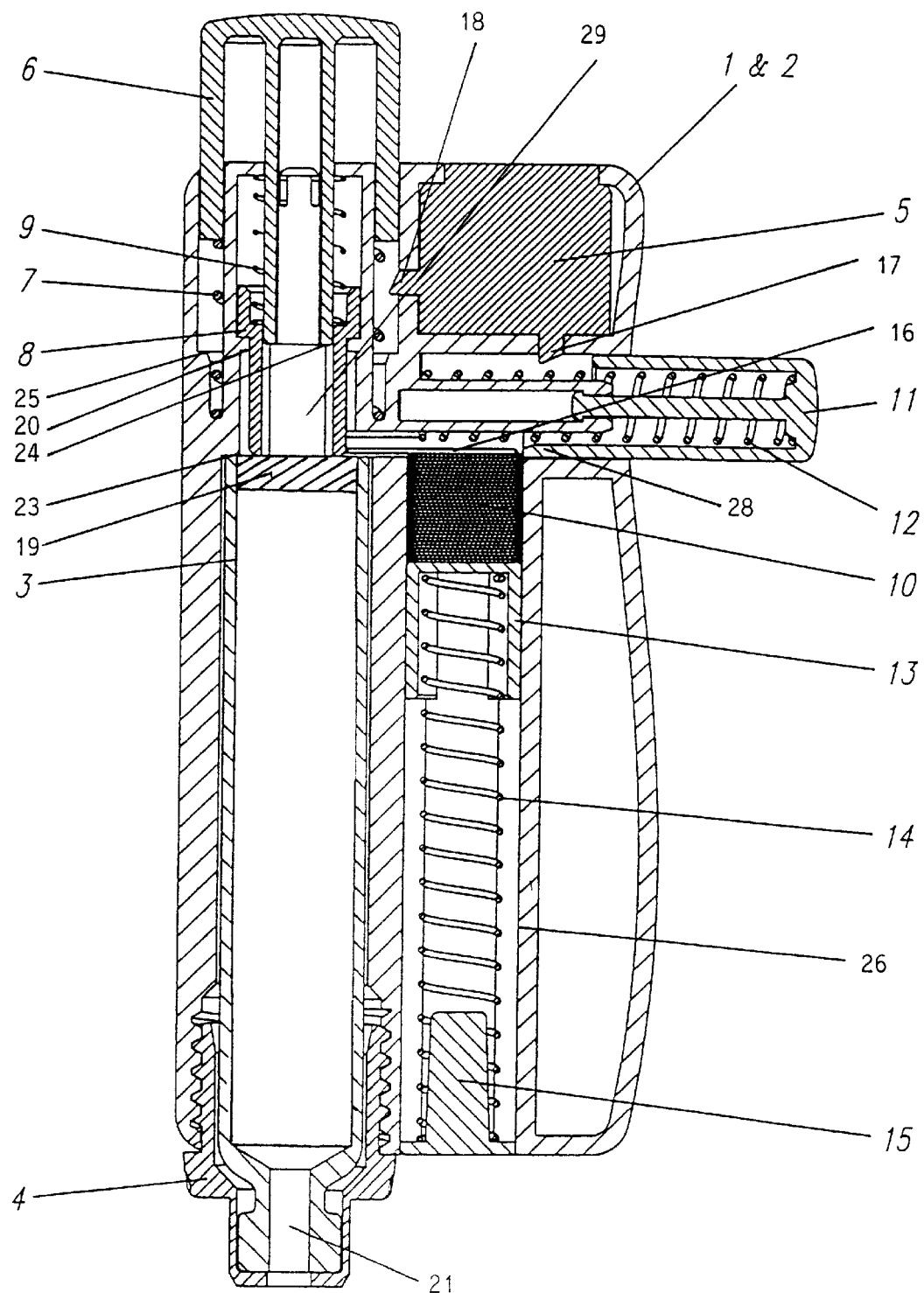
FIG. 2 is a longitudinal section through the device, in a starting position.

FIG. 2 shows the device in a starting position. Product fluid has not yet been delivered from the ampoule 3. A piston 19 which, when shifted in an advancing direction towards an outlet 21 of the ampoule 3, forces product out of the ampoule 3, closes flush with an upper edge 23 of the ampoule 3. No dosing body 10 is situated in a dosing position between the piston 19 and the advancing element 6. The advancing element 6 is held in a starting position by the tensioning element 7 which is formed as a spring. From this starting position, the advancing element 6 can be linearly pressed in the advancing direction, counter to the force of the spring, onto the piston 19, until the advancing element 6 abuts a stopper 25 of the casing. In this position, the advancing element 6 linearly contacts the upper side of the piston 19 via a pressing surface 24. In this delivery position of the advancing element (cf. FIG. 5), the pressing surface 24 of the advancing element is situated in the same plane as the edge 23 of the ampoule 3. If a dosing body 10 is situated between the piston 19 and the advancing element 6, then the dosing body 10 is slid into the ampoule 3 by the advancing element 6 pressing against it, wherein the piston 19 is pressed in the advancing direction.

The height of the stockpile of dosing bodies corresponds to the maximum advancing path of the piston 19. This height can be varied; in the drawing, however, a stockpile of a lesser height is shown. From a lower side of the stockpile, a guiding piece 13 presses the upper side of the stockpile towards a stopper 16. The guiding piece 13 and the dosing body 10 are laterally guided in the magazine 26. A pressure spring 14 situated in the magazine 26 between the guiding piece 13 and a cover 15 presses the stockpile, while elastically giving, against the stopper 16.

A dosing body 10 is formed by a flat lamina. The lamina exhibits a constant thickness. The dosing bodies 10 are round and flattened at two opposing sides. In order to facilitate sliding the dosing bodies 10 over each other into the dosing position, the dosing bodies 10 are chamfered at their front and rear ends with respect to their shifting direction. The chamfers are provided such that each dosing body 10 can easily be slid under other dosing bodies 10 already situated in the dosing position, without catching. One chamfer is formed sloping from an upper covering surface of the dosing bodies, the other is complementarily formed ascending from a lower covering surface (FIG. 4).

Figure 3:
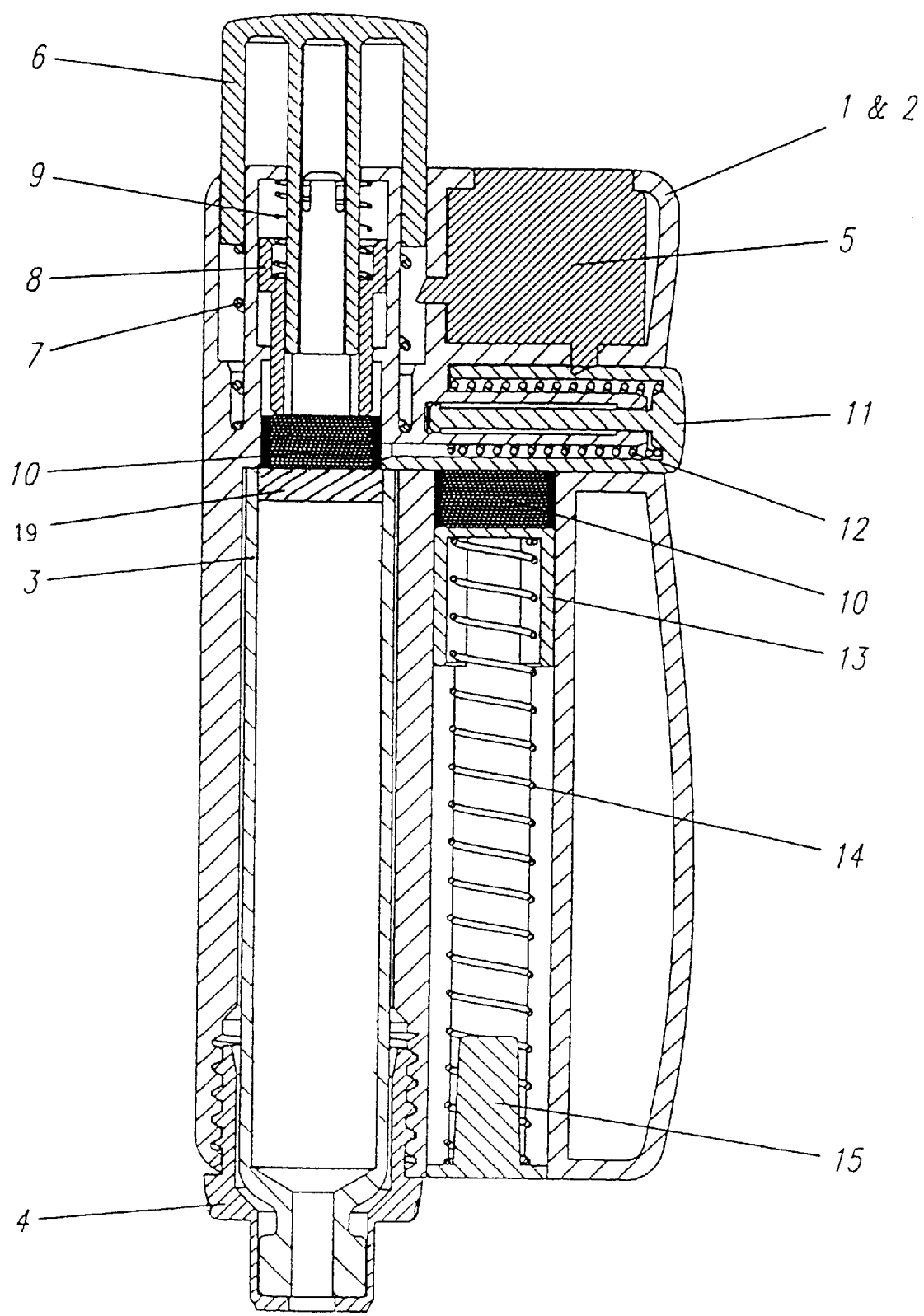
FIG. 3 is a longitudinal section of the device, after a dosage has been set but prior to delivery.
Figure 4:
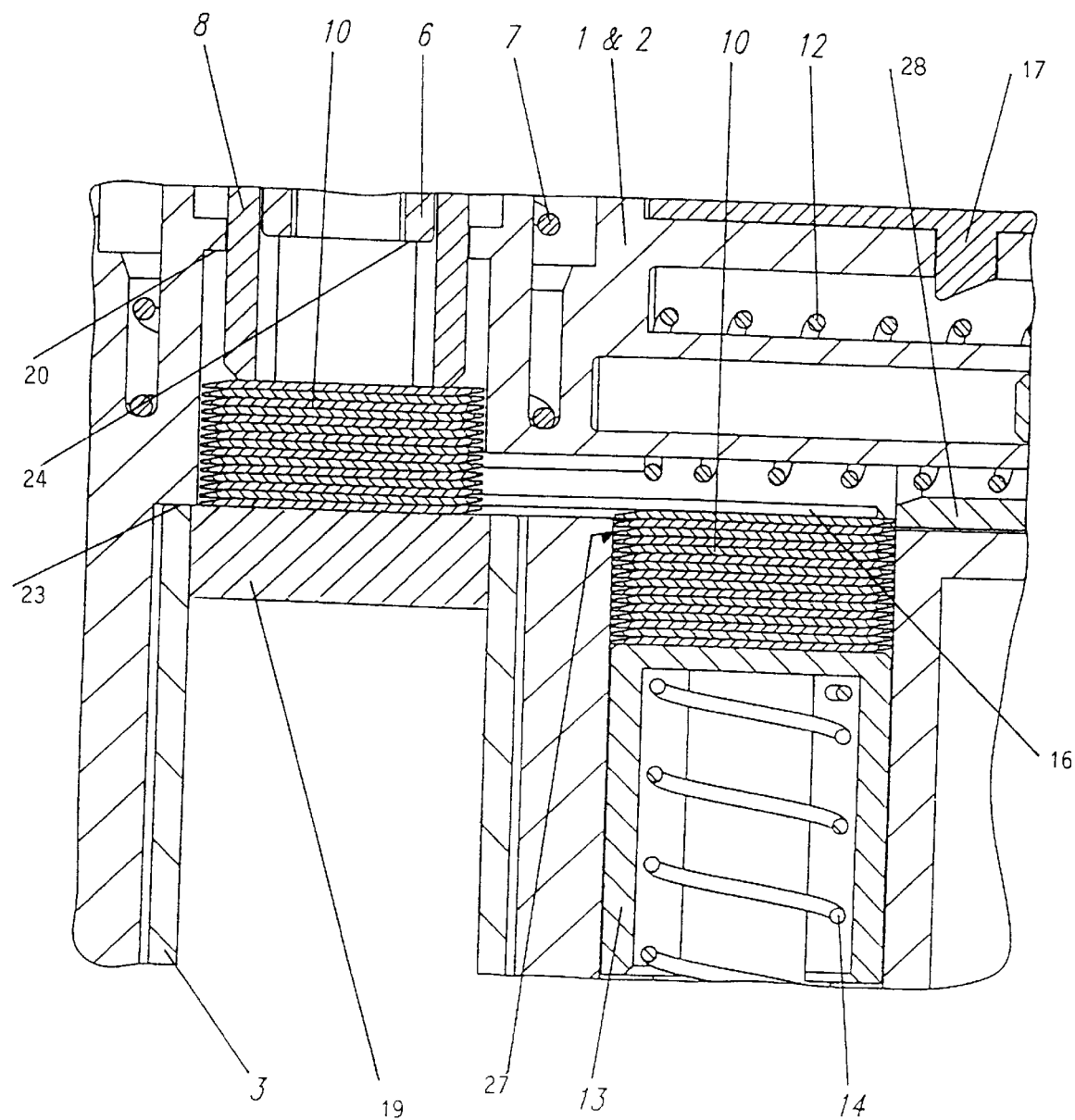
FIG. 4 is a detail of the longitudinal section in accordance with FIG. 3.

FIGS. 3 and 4 show the device and a detail of the device after the product dosage to be administered has been set but prior to delivery. A number of dosing bodies 10 are moved from the stockpile into the dosing position between the piston 19 and the advancing element 6. As can be seen in FIGS. 3 and 4, the stopper 16 holds the stockpile in a position in which only the dosing body 10 abutting the stopper 16 protrudes beyond a lateral guide 27 of the magazine 26. Thus, only this dosing body 10 is released, to be shifted along the stopper 16. The stopper 16 is formed in the shape of a prong. The dosing body 10 is pressed against the stopper 16 at two opposing edges. When the dosing element 11 is advanced perpendicularly to the advancing direction of the piston 19, an area of the dosing element 11 formed as a sliding tongue 28 acts on the facing side of the dosing body 10 and shifts it along the stopper 16. The sliding tongue 28 thus interlocks with the prong-shaped stopper 16. In a similar way to the advancing element 6, the dosing element 11 is held in a starting position by means of its tensioning element 12 which is formed as a pressure spring.

A dosing body 10 is slid by the dosing element 11 into a dosing space 29 (FIG. 2) until it abuts the casing. The dosing space 29 is a space between the piston 19 and the pressing surface 24 of the advancing element 6 in its starting position. In order to fix dosing bodies 10 which have been inserted into the dosing space 29 counter to the advancing direction, a clamp 8 is elastically tensioned towards the piston 19. The clamp 8 is formed as a sleeve which is mounted such that it may be moved in and counter to the advancing direction and overlaps the advancing element 6. The clamping force is generated by a spring 9, the force being less than the static force of the piston 19 in the ampoule 3. A front area of the clamp 8, which presses on the piston 19, is formed chamfered on its outer surface area. A dosing body 10 is slid by the dosing element 11 between the clamp 8 and the piston 19. The clamp 8 thus gives way, counter to the advancing direction of the piston 19 and counter to the force of the spring 9. The dosing body 10 is situated in the dosing position between the piston 19 and the advancing element 6, and is held pre-tensioned by the clamp 8.

A switch or contact 17, connected to a counter 5, is situated in or alongside the shifting path of the dosing element 11. If the dosing element 11 is slid past the contact 17, the counter 5 counts on by one number. The number dosing bodies 10 situated in the dosing position is displayed by a display 22 (FIG. 1). A second switch or contact 18 is situated in the shifting path of the advancing element 6. It serves to re-set the counter 5 to zero during a deliver process. The counter 5 can be an electrical or mechanical counter.

Figure 5:
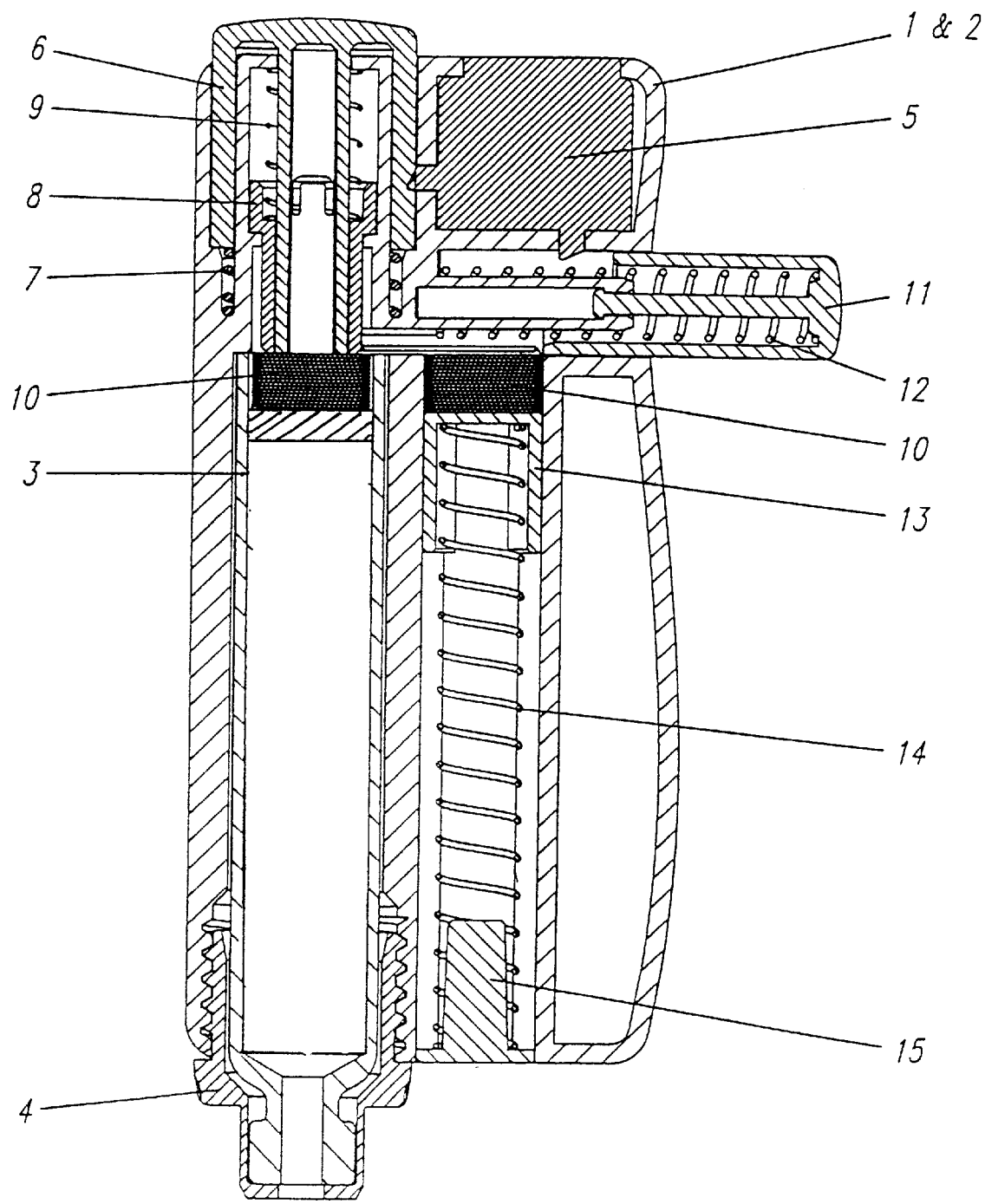
FIG. 5 is a longitudinal section of the device after the dosage has been delivered.

The use of the device of the present invention, or course of an administering process, will now be described. Starting from the starting position of the device in accordance with FIGS. 1 and 2, as many dosing bodies 10 as are required for the desired dosage are each individually moved by the dosing element 11 from the stockpile into the dosing position between the piston 19 and the advancing element 6. FIG. 3 shows the device at the end of the dosing process for an examplary dosage. A number of dosing bodies 10 in the dosing position are guided by the casing, perpendicular to the advancing direction, in alignment with the ampoule 3, and fixed in or counter to the advancing direction by the clamp 8. If the advancing element 6 is shifted in the advancing direction, it presses the dosing bodies 10 out of the dosing position into the ampoule 3 and thus slides the piston 19 in the advancing direction towards the outlet 21 of the reservoir 3, such that the product dosage set is forced out of the reservoir 3. FIG. 5 shows the device in its delivery position after delivery is complete, before it automatically restores itself to the starting position. Dosed administering is complete and another administering can be started when the advancing element 6 has been slid into its starting position by the force of the spring 7.

In the foregoing description, embodiments of the invention, including preferred embodiments, have been presented for the purpose of illustration and description. It is not intended to be exhaustive or to limit the invention to the precise form disclosed. Obvious modifications or variations are possible in light of the above teachings. The embodiments was chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A device for administering an injectable product in doses, including:
   a) a casing comprising a reservoir for the product;
   b) a piston which, when shifted in an advancing direction towards an outlet of the reservoir, forces product out of the reservoir;
   c) a delivery means comprising an advancing element which presses the piston in the advancing direction by a set path length;
   d) and a dosing means comprising a number of dosing bodies and a dosing element, wherein the path length is defined by at least one dosing body which is inserted between the piston and the advancing element by means of the dosing element, before the delivery means is activated.

2. The device as set forth in claim 1, wherein the dosing bodies are slid between the piston and the advancing element perpendicular to the advancing direction of the piston.

3. The device as set forth in claim 1, wherein the dosing bodies are piled loosely one on top of the other between the piston and the advancing element, in the advancing direction of the piston.

4. The device as set forth in claim 1, wherein the dosing bodies are laminae.

5. The device as set forth in claim 1, wherein the dosing bodies are tapered front and back in the shifting direction, for dosing.

6. The device as set forth in claim 1, wherein the dosing bodies are accommodated in a magazine, piled one on top of the other into a stockpile, and wherein, when the dosing element moves perpendicular to the stockpile, it displaces a dosing body away from the stockpile between the piston and the advancing element.

7. The device as set forth in claim 6, wherein the stockpile is pressed against a stopper by a pre-tensioned spring, the stockpile is laterally guided in the magazine, and only a single dosing body, nearest to the stopper, is released for one perpendicular shift.

8. The device as set forth in claim 6, wherein the magazine is laterally offset along the reservoir and the dosing bodies are linearly shifted, perpendicular to the stockpile and perpendicular to the advancing direction of the piston, away from the stockpile between the piston and the advancing element.

9. The device as set forth in claim 1, wherein a dosing body is guided along a stopper in order to be inserted between the piston and the advancing element.

10. The device as set forth in claim 9, wherein, while a dosing body is being inserted between the piston and the advancing element, the dosing element and the stopper are slid one of at least partially over or into each other.

11. The device as set forth in claim 1, wherein one or more dosing bodies are held pre-tensioned in a dosing position between the piston and the advancing element.

12. The device as set forth in claim 1, wherein the delivery means includes a clamp which is pressed in the advancing direction towards the piston by an elastically acting tension force and wherein, when a dosing body is inserted between the piston and the advancing element, the clamp is counter to the advancing direction.

13. The device as set forth in claim 12, wherein the clamp is arranged such that it may be moved relative to the advancing element.

14. The device as set forth in claim 1, wherein the dosing bodies moved into a dosing position between the piston and the advancing element are counted by a counter, and the number of them is displayed by a display.

15. An injection device comprising a casing, a piston, an advancing element which moves the piston a selected path length, and a dosing mechanism comprising a number of dosing bodies and a dosing element operable to move the dosing bodies, wherein the path length is selected by the dosing element moving one or more of the dosing bodies between the piston and the advancing element.

* * * * *